United States Patent [19]

Cuomo et al.

[11] Patent Number: 4,801,431
[45] Date of Patent: Jan. 31, 1989

[54] SLIDE PAIR HOLDER AND ASSEMBLY

[75] Inventors: Carlo Cuomo, Verona; David J. Brigati, Hummelstown, both of Pa.

[73] Assignee: Fisher Scientific Company, Pittsburgh, Pa.

[21] Appl. No.: 32,874

[22] Filed: Mar. 31, 1987

Related U.S. Application Data

[63] Continuation-in-part of Ser. No. 775,864, Sep. 13, 1985, Pat. No. 4,731,335.

[51] Int. Cl.⁴ .............................................. B01L 9/00
[52] U.S. Cl. ..................................... 422/104; 211/41; 350/534; 422/100; 422/102; 436/180
[58] Field of Search ................. 422/99, 100, 102, 104; 436/180; 73/864.72; 350/534; 211/41

[56] References Cited

U.S. PATENT DOCUMENTS

| | | | |
|---|---|---|---|
| 2,119,407 | 5/1938 | Weiskopf | 211/41 |
| 2,488,535 | 11/1949 | Hamburg | 211/41 |
| 2,511,730 | 6/1950 | McClain | 211/41 |
| 2,863,319 | 12/1958 | McLin | 422/100 |
| 3,358,496 | 12/1967 | Farma | 73/864.12 |
| 3,837,795 | 9/1974 | Becker et al. | |
| 4,199,613 | 4/1980 | Johnson | 427/2 |

FOREIGN PATENT DOCUMENTS 1180166 10/1964 Fed. Rep. of Germany.
2152700A 7/1985 United Kingdom.

OTHER PUBLICATIONS

Fisher Scientific Cat. 1983, p. 798.

Primary Examiner—Michael S. Marcus
Attorney, Agent, or Firm—Alan M. Doernberg

[57] ABSTRACT

A holder holding in fixed array:
(a) a plurality of vertically-extending slides each having a vertically-extending face,
(b) a plurality of vertically-extending cover members, each having a vertically-extending face, each face of a vertically-extending slide being spaced by a first distance less than 0.5 mm from a face of a vertically-extending cover member. The holder engages the vertically-extending slides and vertically-extending cover members adjacent to their upper ends in a fixed array with the sample face of each slide being a first distance from a substantially parallel face of a vertically-extending cover member. The lower edge of each slide extends horizontally and is spaced from a substantially parallel horizontally-extending lower edge of a cover member by the first distance. The space between the horizontally-extending lower edges is open. Such an array can contact liquid with the lower edges and draw liquid by capillary action into each gap which is the first distance in thickness, such as treating liquid for samples immobilized on the slide face, cover member face or both.

12 Claims, 3 Drawing Sheets

4,801,431

SLIDE PAIR HOLDER AND ASSEMBLY

This is a continuation-in-part of U.S. Ser. No. 775,864 of Brigati, filed Sept. 13, 1985, copending and commonly-assigned, now U.S. Pat. No. 4,731,335, issued Mar. 15, 1988.

The present invention relates to holders for microscope slides and assemblies of plural pairs of slides in such holders.

In the staining of samples in microscope slides, the slides are generally held vertically extending in rows of parallel slides spaced by distances greater than the (typically 1 mm) thickness of the slides. Holders such as Fisher Scientific Catalog Number 15-185-178 support such slides the side and bottom. A holder is described in U.S. Pat. No. 4,199,613 to Johnson (1980) whereby 50 slides are held in a vertical stack, each slide 200 micrometers above the next slide down. The two end portions of the horizontally-extending extending slides are separated by shims of 200 micrometer thickness. The entire array is enclosed within a housing and liquid is applied down the sides of the slides so as to migrate horizontally into the central 200 micrometer thick gap between each adjacent pair of slides.

SUMMARY OF THE INVENTION

The present invention provides an array of slide assemblies comprising:

(a) a plurality of vertically-extending slides each having a vertically-extending face, (b) a plurality of vertically-extending cover members, each having a vertically-extending face, each face of a vertically-extending slide being spaced by a first distance less than 0.5 mm from a face of a vertically-extending cover member, and (c) engagement means for holding the vertically-extending slides and vertically-extending cover members adjacent to their upper ends in a fixed array with the sample face of each slide being a first distance from a substantially parallel face of a vertically-extending cover member and with the lower edge of each slide extending horizontally and being spaced from a substantially parallel horizontally-extending lower edge of a cover member by the first distance, the space between the horizontally-extending lower edges being open.

DETAILED DESCRIPTION OF THE INVENTION

Figure 1:
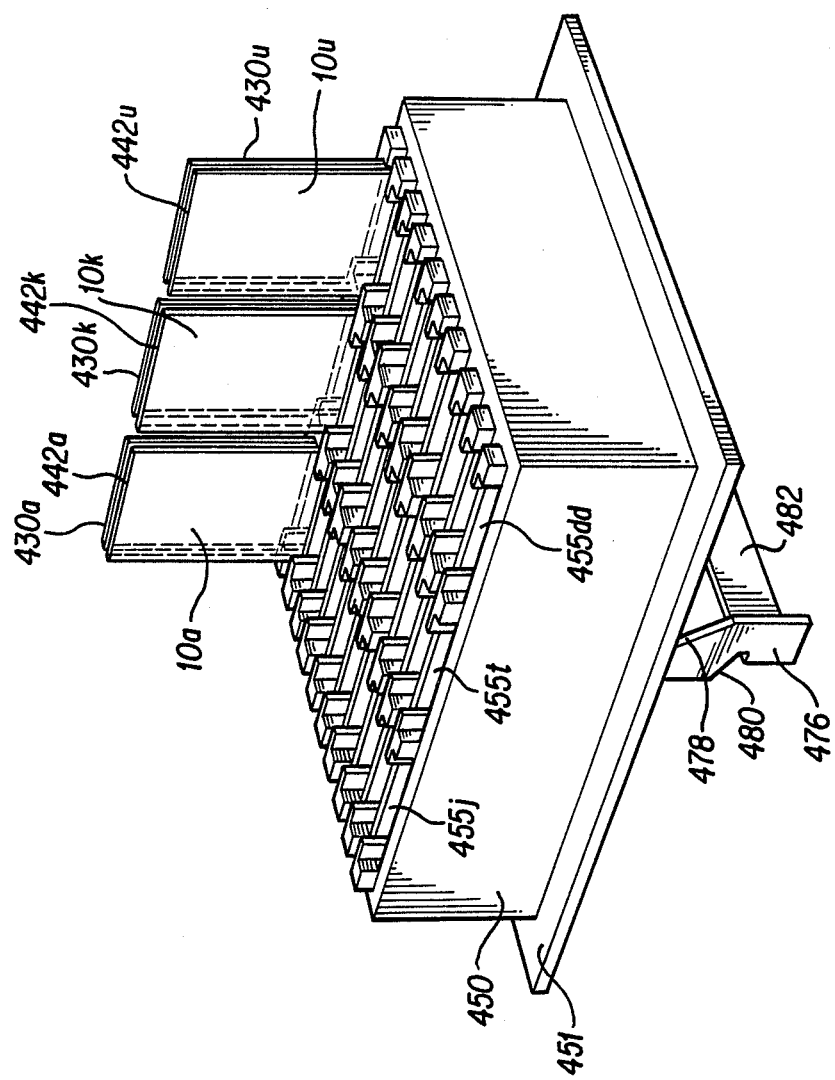
FIG. 1 is a perspective bottom view of a partially filled holder according to a first embodiment of the present invention.

FIG. 1 shows a holder partially filled with slide pairs according to a first embodiment of the present invention.

The main body 450 of the slide holder shown in FIG. 1 is shaped as a rectangular solid with, as described below, a series of slots formed in its lower face for receiving slide pair assemblies.

Alternatively, the slide pairs may be held in a holder where the series of slots formed at its lower face are collapsible and can be tightened upon the top portions of the slide pair assemblies using, for example, a substantial modification of the slide rack of FIG. 1 of U.S. Pat. No. 4,199,613 of Johnson in which the "shims" are significantly thicker and used to separate slide pair assemblies and not to produce capillary action.

Because the slide holder is inverted in FIG. 1, compared to its configuration in use, for the insertion of slide pairs, this bottom face appears on top. In the following description, relative positions in use (e.g., slots in the bottom face) will be described.

A plate 451 is above main body 450 (as a flange) in both horizontal directions so as to cover a large rectangular crosssectional area than the rectangular cross-sectional area of main body 450. An arm 476 extends vertically upward from one side of plate 451, with two angled portions 478 and 480. A similar arm 476, with angled portions 478 and 480, extends vertically upward from the opposite side of plate 451, but is hidden from view. A horizontal bar 482 connects the two arms 476.

Formed in the bottom face of main body 450 are ten long slots, each extending vertically downward from plate 451 and in a horizontal direction 90° relative to horizontal bar 482. These ten long slots are each divided by partitions into three slots, for a total of thirty slots. The nearest three slots are designated 455j, 455t and 455dd in FIG. 1, each such slot being at the near end of a row of ten slots. Sample-bearing slides 10a, 10k and 10u are shown extending out of the slots at the far end of each of the three rows. As illustrated by facing slide 430u, a facing slide is inserted with each sample-bearing slide in a common slot. The bottom edges of each sample-bearing slide and the adjacent facing slide defines a lower end of a gap, shown as lower end 442a, 442k and 442u for slides 10a, 10k and 10u, respectively. Each individual slide pair appears in cross-section substantially as shown in FIG. 2B of U.S. Ser. No. 775,864, and as described briefly below.

If thirty sample-bearing slides are to be treated, then the remaining slots shown in FIG. 1 (up to slots 455j, 455t and 455dd) are filled and the entire slide holder assembly inverted. To keep track of the various slides, either visually- or machine-readable indicia may be present or applied (e.g., on a frosted portion of each slide remote from the sample) so as to be read before and after treatment, or (if the indicia are properly placed, e.g., just above the sample location) also while the slides are in the holder. Additionally, the holder may be indexed numerically to ease the localization of individual slides without taking them out of the holder and to ease reagent handling by having corresponding numbers denoting the specific holes in the droplet holder pictured in FIGS. 3B and 7 of U.S. Ser. No. 775,864 with which the slide pair assembly interacts.

The holder is then lowered into a bracket of a slide staining instrument, with the bracket being the width of horizontal bar 482 along angled portions 478 of arms 476, until the slide assembly is held and aligned (vertically and horizontally) by the engagement of the bracket with horizontal bar 482 and arms 476. The machine can now conduct the assembly through a series of stations as described in relation to FIG. 6 of U.S. Ser. No. 775,864. Alternatively, the holder's horizontal bar 482 may be engaged manually and thereby advanced.

Each slide pair fitted into the slots shown in FIG. 1 should be provided with a shim or the like to maintain the capillary gap (e.g., between 10u and slide 430u) and a rubber protuberance or the like to compress the slide pair within the slot. In FIGS. 1A–1C of U.S. Ser. No. 775,864, the shim is illustrated as tape; in FIGS. 2A–2E of U.S. Ser. No. 775,864, the shim is illustrated as a glass coverslip of 150, 200 or 250 miccrometer (0.15, 0.20 or 0.25 mm) thickness. In FIG. 4 of U.S. Ser. No. 775,884 and in FIG. 2D, below, the shim is a coating on one or both slides of the slide pair. As indicated in U.S. Ser. No. 775,885, the thickness of the shim and, therefore, the capillary gap below the shim is in general about 50 to about 500 micrometers. Preferably, that thickness is about 100 to about 250 micrometers (especially about 150 to about 200 micrometers).

The compression can be caused by a rubber protuberance on the top exterior face of either the first slide (e.g., slide 10u), the facing slide (e.g., slide 430u) or both. The shim, if a cover slip, or the like, can be pre-attached to the facing slide (e.g. 430u) or can be sandwiched without pre-attachment between the slide pair (e.g., between the top of slide 10u and the top of slide 430u). The rubber protuberances can also be present on the interior of the slots.

Figure 2A:
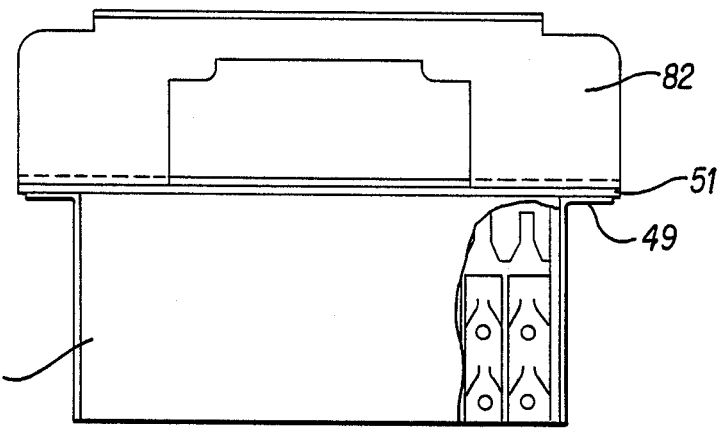
FIG. 2A is a side elevational view, partially in section, of a holder according to a second embodiment of the present invention.
Figure 2B:
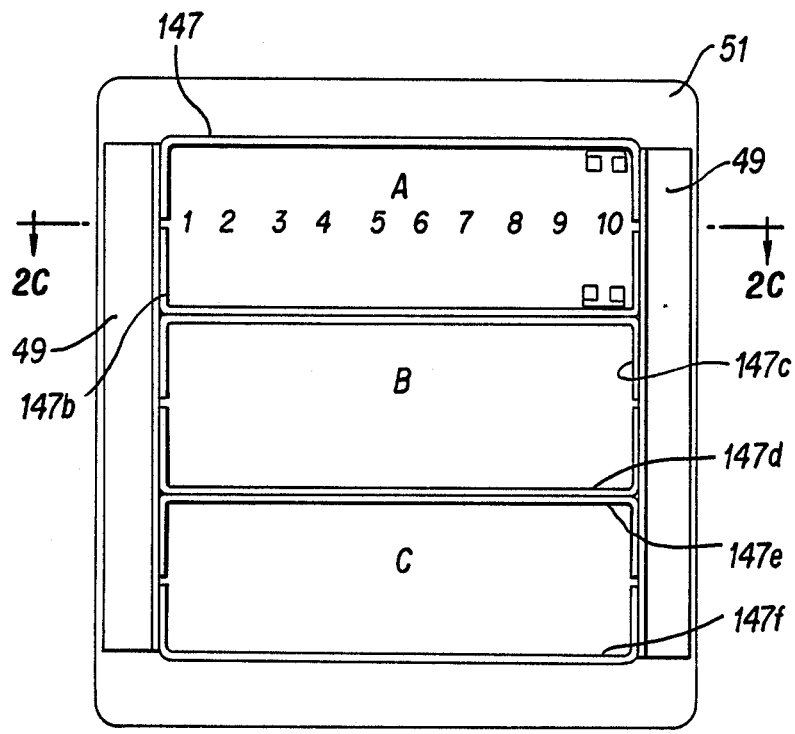
FIG. 2B is a bottom plan view of the slide holder of FIG. 2A.

FIGS. 2A and 2B are side and bottom views of a slide holder according to a second embodiment of the present invention. A cover 51 is provided as a flat plate with indicia (letters A, B and C, numerals 1 through 10) on the bottom as described below. Above the cover 51 is a handle 82 for manual movement or attachment to an arm of a slide stainer instrument. On the front and back sides of cover 51 are angle brackets 49 which have a minor portion flush with and below cover 51 and a major portion extending downward. Six divider brackets 147a through 147f extend downward from cover 51 between the major portions of angle brackets 49 and divide the space between such major portions laterally into three regions of rectangular solid shape: region A between bracket 147a and bracket 147b, region B between bracket 147c and bracket 147d, and region C between bracket 147e and bracket 147f. Divider bracket 147b is flush against bracket 147c; divider bracket 147d is flush against divider bracket 147e. Each divider bracket has a major portion extending downward and forwardly and two minor portions extending downward and (for brackets 147b, 147d and 174f) leftward or (for brackets 174a, 147c and 147e) rightward taking the left side of FIG. 2B as the front of the holder. The minor portions are flush with and interior of the major portions of angle brackets 49.

Figure 2C:
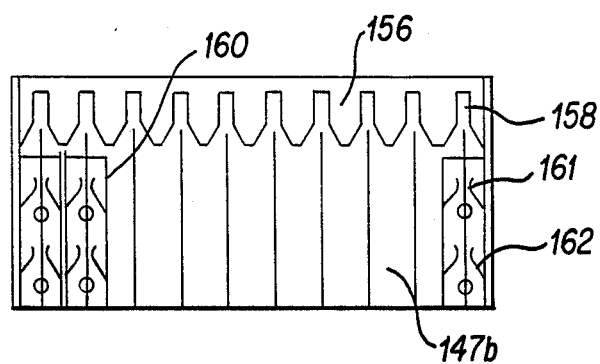
FIG. 2C is a side elevational view, in section, along line 2C—2C in FIG. 2B.

FIG. 2C shows the left (open) surface of the major portion of divider bracket 147b. The left (open) surfaces of the major portions of divider brackets 147d and 147f and the right (open) surfaces of the major portion of divider brackets 147a 147c and 147e would appear the same. An alignment strip 156 which is 0.093 inch (2.4 mm) in thickness is flush against the top portion of divider bracket 147b. Ten evenly spaced slots 158 are formed in the lower edge of alignment strip 156 and taper down to a width of 0.093 inch (2.4 mm). Ten pairs of upper clips 161 and lower clips 162 are fixed to divider bracket 147b below alignment strip in an arrangement whereby a vertical channel extends from each recess 158 through an upper clip 161 and a lower clip 162.

Figure 2E:
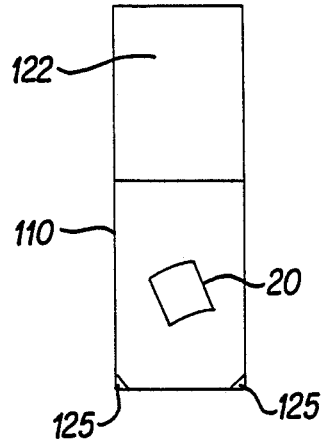
FIG. 2E is a front elevational view of one of the slides inserted in FIG. 2D into the holder.
Figure 2D:
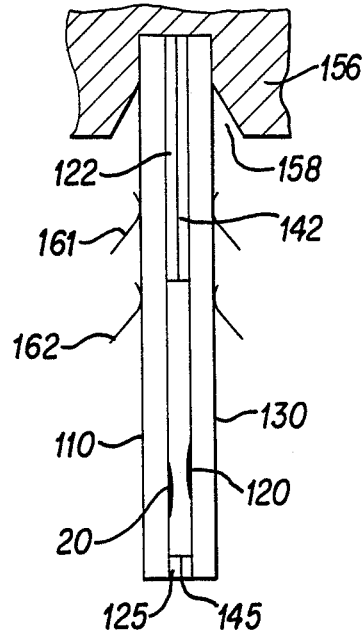
FIG. 2D is an enlarged side elevational view, taken along a segment of line 2C—2C, also showing a slide pair inserted into the holder.

FIG. 2D shows a slide pair received within such a channel. The slide pair consists of a first microscope slide 110 and a second or facing microscope slide 130. Each slide is typical 1 mm in thickness, 1 inch (25.4 mm) in width and 3 inches (76.2 mm) in height. The width of the slides extends between divider brackets (e.g., from divider bracket 147a to divider bracket 147b) as seen in FIG. 2B. Each of regions A, B and C accordingly can accommodate ten slide pairs. Indicia (numerals 1 through 10) are provided on the bottom face of the cover 51, either in one region (e.g., region A as can be seen in FIG. 2B) or in all three regions.

Looking again at FIG. 2D, the top five-twelfths of first slide 110 is coated on the right face by upper coating 122, typically to a thickness of 80 micrometers. The top five-twelfths of second slide 130 is coated on the left face by upper coating 142, typically to a thickness of 80 micrometers. Upper clip 161 and lower clip 162 press the portions of slides 110 and 130 against each other above the middle and near the bottom of the 1.25 inch (31.8 mm) portions corresponding to coatings 122 and 142. Accordingly, the remaining portions of slides 110 and 130 (the lower 1.75 inch or 44.4 mm of each) are separated by a gap 160 micrometers in thickness, 44.4 mm in height and 25.4 mm in width. If no further coatings are provided, the entire 25.4 mm of the lower edge of this gap would be open.

As shown in FIGS. 2D and 2E, two lower corners of slide 110 (slide 130 is similar) are coated with an 80 micrometer thick coating which is triangular in shape, so as to extend 4 mm up and 4 mm in from each corner along the side and bottom edges of the first slide 110. The triangular coating on first slide 110 is labeled 135; the triangular coating on second slide 130 is labeled 145. Accordingly, the 160 micrometer thick gap is maintained, but flares out at a 45 degree angle from a width of 17.4 mm at the lower edge to a width of 25.4 mm at a height of 4 mm above such lower edge.

In use, up to thirty slide pairs (with samples on one or both slide of each pair) are inserted into the holder. The holder is then lowered onto a series of liquids, typically liquid reagents. Each liquid may be in the form of a bath or sheet, in the form of individual round droplets supported on a droplet holder (see FIG. 7 of U.S. Ser. No. 775,864) or in the form of laterally-extending aliquots on a modified droplet holder (see FIGS. 3A, 3B and 3C of an application of Brigati, U.S. Ser. No. 032,875, filed Mar. 31, 1987, commonly-assigned and also a continuation-in-part of U.S. Ser. No. 775,864). Liquid rises by capillary action into the gap between each first slide 110 and the adjacent second or facing slide 130. See FIG. 3C of U.S. Ser. No. 775,864. After the appropriate time of liquid contacting sample on one or both slides the slide assembly is then lowered onto a flat blotter. Liquid is then drawn by capillary action into the blotter so as to evacuate each capillary gap, as shown in FIG. 3D of U.S. Ser. No. 775,864. If a droplet holder is used for the particular step, then the process can be individualized so as to treat different slide pairs with different liquids (e.g., different primary antibodies, nucleic acid probes, enzymes or chromogens). After evacuation, the slide assembly can then be lowered over a liquid representing the next step of the process. Conveniently, indicia (letters A, B and C and numerals 1 through 10) can be provided on each droplet holder to correspond to indicia on the bottom of cover 51. It is also contemplated that the plurality of slides in the holder may be as many as 100 or more slide pairs.

What is claimed is:

1. An array of slide assemblies comprising:
   (a) a plurality of vertically-extending slides, each having a vertically-extending face and a lower edge,
   (b) a plurality of vertically-extending cover members, each having a vertically-extending face and a lower edge, each face of a vertically-extending slide being spaced by a first distance less than 0.5 mm from a face of an adjacent vertically-extending cover member, each slide and adjacent cover member together comprising a slide assembly, and
   (c) engagement means for holding the slide assemblies of vertically-extending slides and vertically-extending cover members adjacent to their upper ends in a fixed array with the lower edge of each slide extending horizontally and being spaced from a substantially parallel horizontally-extending lower edge of the adjacent cover member of the same slide assembly by the first distance, the space between the adjacent horizontally-extending lower edges of a slide assembly being open.

2. The array of claim 1 wherein the first distance is between about 50 and about 500 micrometers.

3. The array of claim 1 wherein a coating on an upper portion of the substantially parallel face of the cover member of each slide assembly contacts an upper portion of the vertically-extending face of the slide of that slide assembly.

4. The array of claim 1 wherein a first coating is provided on an upper portion of the substantially parallel face of the cover member of each slide assembly, a second coating is provided on an upper portion of the vertically-extending face of the slide of that slide assembly and each first coating is in contact with the adjacent second coating to define the first distance.

5. The array of claim 1 wherein the first distance is about 100 to about 250 miccrometers.

6. The array of claim 5 wherein the first distance is about 150 to about 200 micrometers.

7. The array of claim 1 wherein the engagement means comprises a plurality of downwardly opening slots and wherein a horizontal upper end of each slide assembly is inserted in one of the downwardly opening slots.

8. The array of claim 7 wherein a first plurality of the downwardly opening slots are arranged in a horizontal row in the engagement means, and a first plurality of slide assemblies are inserted in the first plurality of slots, each lower edge of each slide and cover member of the first plurality of slide assemblies extending horizontally parallel to each other lower edge of the first plurality of slide assemblies and being arranged in a row extending horizontally normal to each lower edge of the first plurality of slide assemblies.

9. The array of claim 8 wherein the engagement means further comprises a second plurality of the downwardly opening slots, each lower edge of each slide and cover member of the second plurality of slide assemblies extending horizontally parallel to each other lower edge of the second plurality of slide assemblies and being arranged in a row extending horizontally normal to each lower edge of the second plurality of slide assemblies and extending horizontally parallel to the row of the first plurality of slide assemblies.

10. The array of claim 1 wherein a shim of the thickness of the first distance is between the upper end of each vertically-extending slide and the upper end of each vertically-extending cover member of a slide assembly.

11. The array of claim 10 wherein the shim is sandwiched between the slide and the cover member of a slide assembly.

12. The array of claim 10 wherein the shim of each slide assembly is attached to the cover member of that slide assembly.

* * * * *